US006461665B1

(12) United States Patent
Scholander

(10) Patent No.: US 6,461,665 B1
(45) Date of Patent: Oct. 8, 2002

(54) PROCESS FOR PREPARING SURFACE MODIFICATION SUBSTANCES

(75) Inventor: Elisabeth Scholander, Uppsala (SE)

(73) Assignee: Carmeda AB, Stockholm (SE)

( * ) Notice: Subject to any disclaimer, the term of this patent is extended or adjusted under 35 U.S.C. 154(b) by 0 days.

(21) Appl. No.: 09/763,873

(22) PCT Filed: Sep. 8, 1999

(86) PCT No.: PCT/NO99/00277

§ 371 (c)(1),
(2), (4) Date: Feb. 28, 2001

(87) PCT Pub. No.: WO00/13718

PCT Pub. Date: Mar. 16, 2000

(30) Foreign Application Priority Data

Sep. 9, 1998 (NO) ............................................. 19984143

(51) Int. Cl.[7] .............................. A61F 2/02; A61F 2/06; A61L 17/00; B05D 1/36
(52) U.S. Cl. .................... 427/2.24; 427/2.25; 427/2.28; 427/2.3; 427/2.31; 427/301; 427/407.1; 427/409; 623/1.1; 623/1.43; 623/1.44; 623/1.45; 623/1.46

(58) Field of Search ................................. 427/2.24, 2.25, 427/2.28, 2.3, 2.31, 301, 407.1, 409; 623/1.1, 1.43, 1.44, 1.45, 1.46

(56) References Cited

U.S. PATENT DOCUMENTS 5,049,403 A * 9/1991 Larm et al. ..................... 427/2
5,679,659 A * 10/1997 Verhoeven et al. ........... 514/56

FOREIGN PATENT DOCUMENTS

| EP | 0 086 186 | 8/1983 | |
| EP | 0 200 295 | * 2/1986 | ........... A61L/33/00 |
| EP | 0 200 295 | 12/1986 | |
| EP | 0 565 862 | 10/1993 | |
| EP | 0 832 618 | 4/1998 | |
| WO | WO9707834 | 3/1997 | |

* cited by examiner

Primary Examiner—Shrive P. Beck
Assistant Examiner—Jennifer Kolb Michener
(74) Attorney, Agent, or Firm—Nixon & Vanderhye

(57) ABSTRACT

The present invention relates to a process for preparing surface modifications having an improved antithrombogenic activity, whereby the improvement is achieved by treating heparin at a temperature above 40° C. or a pH in the rage of 9–14 or in contact with nucleophilic catalysts before attaching said heparin to the surface to be modified.

10 Claims, No Drawings

PROCESS FOR PREPARING SURFACE MODIFICATION SUBSTANCES

This application is a 371 of PCT/NO99/00277, filed Sep. 8, 1999.

The present invention relates to a method for preparing an improved non-thrombogenic surface modification for surfaces intended for contact with body fluids or tissue, or components therefrom.

BACKGROUND OF THE INVENTION

When the surface of a medical device such as a catheter tube, blood oxygenator, stent or the like is placed in the body, or in contact with body fluids, a number of different reactions are set into motion, some of them resulting in the coagulation of the blood on the device surface. In order to counteract this serious adverse effect, the well-known anticoagulant compound heparin has for a long time been administered systemically to patients before medical devices were placed in their body or in contact with their body fluids in order to ascertain an antithrombotic effect.

Thrombin is one of several coagulation factors, all of which work together to result in the formation of thrombus at a non-self surface in contact with the blood. Antithrombin is the most prominent coagulation inhibitor. It neutralises the action of thrombin and other coagulation factors and thus restricts or limits blood coagulation. Heparin dramatically enhances the rate whereby antithrombin inhibits coagulation factors.

However, systemic treatment with high doses of heparin is often associated with serious side-effects of which bleeding is the predominant. Another rare but serious complication of heparin therapy is the development of an allergic response called heparin induced thrombocytopenia that may lead to both bleeding and arterial thrombosis. Heparin treatment also requires frequent monitoring of plasma levels and dose adjustments accordingly. Heparin reversal with protamin is another complication.

Therefore solutions have been sought where the need for a systemic heparinisation of the patient would be unnecessary. It has been considered likely that this could be achieved through a surface modification using the anti-coagulative properties of the heparin. Thus, different technologies have been developed where a layer of heparin is attached to the surface of the medical device whereby the surface is rendered non-thrombogenic.

Heparin is a polysaccharide compound carrying negatively charged sulphate groups on the saccharide units. Ionic binding of heparin to polycationic surfaces was thus attempted, but these surface modifications suffered from lack of stability resulting in lack of function, as the heparin leached from the surface.

Thereafter different surface modifications have been prepared wherein the heparin has been covalently bound to groups on the surface.

PRIOR ART

One of the most successful processes for rendering a medical device non-thrombogenic is achieved through covalently binding a heparin fragment to a surface modified surface of the medical device. The general method and improvements thereof are described in the following European patents: EP-B-0086186, EP-B-0086187 and EP-B-0495820.

These patents describe the preparation of surface modification substrates which are achieved through firstly, a selective cleavage of the heparin polysaccharide chain through nitrous acid oxidation leading to the formation of terminal aldehyde groups. Secondly, an introduction of one or more surface modifying layers carrying amino groups on the surface of the medical device, and thereafter the aldehyde groups on the polysaccharide chain are reacted with primary amino groups on surface modifying layers followed by a reduction of the intermediate Schiff's bases to stable secondary amine bonds with for instance cyanoborohydride.

This technology has made it possible to prepare stable and well-defined antithrombogenic surface modifications for medical devices.

There are known many other surface modification which claim to achieve similar or even better results, such as for instance described in EP-A-0200295 (U.S. Pat. No. 4,600, 652, U.S. Pat. No. 6,642,242, ) based on substrates having a layer of a polyurethane urea to which heparin modified to contain aldehyde groups through oxidation with nitrous acid or periodate, may be bound by covalent links.

A similar technology is described in EP-A-0404515, where the substrate surface is coated with an amine rich fluorinated polyurethane urea before immobilisation of an antithrombogenic agent, such as an aldehyde-activated heparin.

Another antithrombogenic surface modification which may be mentioned is described in EP-B-0309473. The surface of the device is modified through the coating with a layer of lysozyme or a derivative thereof to which heparin is adhered.

Yet another surface modification for producing antithrombogenic articles is described in U.S. Pat. No. 4,326,532. In this case, the layered antithrombogenic surface comprises a polymeric substrate, a chitosan bonded to the polymeric substrate and an antithrombogenic agent bonded to the chitosan coating. Japanese Patent Laid-Open No. 04-92673 relates to an antithrombogenic hemofilter also using a chitosan layer for binding heparin.

In EP-A- 0481160 it is described antithrombogenic materials useful for coating medical articles, which material comprises an anticoagulant bound to processed collagen.

Another process for preparing antithrombogenic surfaces is described in WO97/07843 wherein the heparin is admixed with sufficient periodate not to react with more than two sugar units per heparin molecule and this mixture is added to a surface modified substrate of a medical device, which surface modification contains amino groups.

This listing of prior art processes for preparing antithrombogenic surfaces is by no means complete, and it is a clear indication that it is difficult to prepare such coated medical articles which exhibit the properties necessary for successful use in patients, namely a sufficient and long-lasting high antithrombogenic activity, stability of the coating and no adverse changes of the properties of the substrate to be coated.

Therefore there is still a need in the art for improvements of the antithrombogenic coatings, which will render the medical articles thereby coated non-thrombogenic in a stable, reliable and reproducible manner and with a strong and lasting antithrombogenic effect.

DEFINITION OF THE INVENTION

A main object of the present invention is to improve the antithrombogenic activity of surface immobilized heparin. This and other objects are achieved by the invention as defined in the attached claims.

Thus, it has now surprisingly been found that it is possible to further improve the antithrombogenic activity of known surface modifications through a simple and inexpensive procedure. The improvement can be measured as a higher heparin bioactivity when the heparin treated according to the invention is attached to a surface.

The present invention relates to a process for preparing surface modifications having an improved antithrombogenic activity, whereby the improvement is achieved by treating heparin at elevated temperature or at elevated pH or in contact with nucleophilic catalysts such as amines, alcoholes, thiols or immobilized amino, hydroxyl or thiol groups before attaching said heparin to the surface to be modified.

As will appear from the prior art mentioned, there are known many different methods for producing a surface modifying layer carrying active groups to which a heparin can be bound or attached, and the heparin prepared according to the present invention and having superior antithrombogenic properties may be used in connection with any prior art method of preparing layers to which heparin can be bound.

Optionally the medical device oh which the surface modification is to be introduced, may be produced from a material or materials, whereby active functional groups are directly available on the surface, without the need for the introduction on the surface of a further layer carrying functional groups to which heparin can be bound. The heparin prepared according to the present invention and having superior antithrombogenic properties may be used in connection with such materials, too.

The process of this invention may be described more generally to include different materials carrying functional groups or different prior art methods of treating the surface in order to make available groups by which heparin, optionally treated to contain for instance aldehyde, carboxylic acid or amino groups, can be attached to that surface, preferably by covalent links.

Thus, such a method for producing a surface modification having an improved non-thrombogenic activity will at least comprise reacting (A) functional groups on a surface to be rendered non-thrombogenic, with (B) heparin, modified to contain complementary functional groups, so as to form covalent bonds, whereby said heparin is activated to enhance its activity when surface bound, in a step before reacting (A) with (B), through a procedure selected from the following group of procedures:

(i) heating in the range from 40° C. to the boiling temperature of the solvent;

(ii) treatment at an elevated pH, i.e. in the range of pH 8–14;

(iii) treatment with nucleophilic catalysts.

Some of the procedures maybe combined to give the same or even an enhanced activity of the surface bound heparin. Thus the procedure (i) may advantageously be combined with either procedure (ii) or (iii).

The term "nucleophilic catalysts" is used to indicate that no actual chemical reaction takes place between the heparin and the nucleophilic catalyst used in the procedure. Examples of compounds usable as "nucleophilic catalysts" according to the present invention are amines, such as ammonium acetate ($NH_4Ac$) or other nitrogen containing compounds such as amino acids and aliphatic or cyclic organic compounds; hydroxyl containing compounds, such as alcoholes; sulfhydryl containing compounds such as thiols . Other possible nucleophilic catalysts according to this invention are polymeric compounds carrying amino, hydroxyl or sulfhydryl groups, such as for instance polethylene imine. Other examples of possible nucleophilic catalysts according to the invention comprise immobilized amino-groups, hydroxyl-groups or thiols, as found on ion exchange substrates or substituted chromatography gels, as will be well-known for persons skilled in the art. It is most preferred to use nitrogen containing nucleophilic catalysts, such as free amines or surface immobilized amines.

The complementary groups in (B) above, are meant to relate to the functional groups mentioned under (A), with the understanding that these two groups must be capable of reacting so as to form covalent bonds. One examples of groups which form covalent bonds are amino and aldehyde groups, and in that case the reaction scheme above must be followed by a further step of stabilising the thereby formed Schiff's base. A person skilled in the art will be aware of other such pairs of functional groups that can form covalent bonds.

The process according to this invention for preparing a surface modification on medical substrates that do not carry functional groups on their surface, may more detailed be described as follows:

(a) treating the surface to be modified so as to form a layer comprising functional groups on the surface, (b) treating heparin, modified to contain complementary functional groups according to the prior art, in a further step selected from the following group of procedures:

(i) heating in the range from 40° C. to the boiling temperature of the solvent (ii) treatment at an elevated pH, i.e. in the range of pH 8–14;

(iii) treatment with nucleophilic catalysts to enhance the activity of the heparin when surface bound, and (c) reacting the layer resulting from step (a) with heparin modified according to step (b) to immobilize the heparin with covalent bonds to the surface.

The layer in step (a) above may be formed using different compounds, such as polymeric compounds like polyurethanurea, polyamine such as polyethyleneimine, chitosan or other polysaccharides or polymers containing reactive functional groups. Alternatively, it is possible to use different layers of polymeric compounds, for instance two of opposite charges, so as to achieve a layer of a certain thickness or texture. In this case the final layer must carry free active groups which can be reacted with the complementary groups of the heparin. The polymers may optionally be cross-linked in the first layers.

Different examples of methods by which a surface of a substrate may be modified will also be apparent from other prior art documents, and it is referred to the descriptions and examples included in such patents and other publications for the detailed working instructions in order to prepare such surface modifications.

The substrates which are most likely to benefit from heparin modified with the processes according to the present invention are medical devices such as oxygenators, blood filters and blood pumps, catheters and tubing and implants such as stents, vascular grafts and heart valves.

Thus the surfaces which are treated may be polymers, glass, metal, natural fibre materials, ceramics or any other material which possesses the right properties for the intended use, as is known to a person skilled in the art.

In a most preferred manner, the first part of the process is conducted as described in EP-B-0086186, EP-B-0036187 or EP-B-0495820 or WO97/07834, and generally comprises the following steps:

(a) adding to the surface to be modified a layer of a polymer comprising amino groups, and b) optionally cross-linking the layer of step (a) with a bifunctional cross-linking agent;

(c) adding to the layer of step (b), a layer of an anionic polymer;

(d) optionally repeating the steps (a), (b) and (c) at least one time, (e) followed by a final step (a), and (f) modifying heparin through nitrous acid or periodate oxidation to comprise aldehyde groups.

Further the process is characterised by the following step which is new and distinctly different compared to the prior art:

(g) treating the aldehyde heparin in water solution in a further step selected from the following group of procedures:
  (i) heating in the range from 40° C. to the boiling temperature of the solvent;
  (ii) treatment at an elevated pH, i.e. in the range of pH 8–14;
  (iii) treatment with nucleophilic catalysts to enhance the activity of the heparin when surface bound.

The process is then preferentially continued as described by the prior art listed above by:

(h) reacting the layer resulting from step (a) or (e) with the further treated aldehyde heparin from step (g).

The surface modified substrates prepared according to this invention are also encompassed by the present invention.

The procedures (i), (ii) and (iii) may be performed in any solvent, but it is most preferred to perform them in aqueous solution, but in special circumstances, it may be suitable to use organic solvents, optionally together with complex builders, or mixtures of aqueous and organic solutions.

The time needed for the heating procedure (i) is not crucial. Presumably, the activation achievable will depend on the combination of time and temperature. Thus, in one embodiment the temperature is in the range 40–80° C. and more preferred 50–70° C. In a second embodiment it is kept at 60° C.

The procedure (ii) is performed at pH 8–14, more preferred pH 8–12. It is more suitable to use the pH range of 9–11.

Advantages

Through the present invention the following advantages can be achieved:

improved nonthrombogenic activity, and as a result thereof
  sufficient non-thrombogenicity can be obtained with lower quantities of immobilized heparin. This is especially important for material and devices associated with difficulties to immobilize large amounts of heparin.
  higher non-thrombogenicity can be obtained with the same amount of immobilized heparin. This is especially important in applications with strong thrombogenic stimuli e.g. in situations with low blood flow and applications like catheters and vascular grafts with narrow lumen or in cases where the patient otherwise would require additional systemic heparinization.

The present invention is explained more closely in the examples below.

EXAMPLE 1

Heparin of pharmacopoeia quality was treated with nitrous acid, essentially as described in EP B-0086186. After the oxidation the reaction solution was divided into four parts (each 60 ml) which were treated according to one of the following steps:

1. Neutralized with 4M NaOH to pH 7.
2. Adjusted to pH 2.5 with 2M HCl and kept at 40° C. for 1 hour, then neutralized with 4M NaOH to pH 7.
3. Adjusted to pH 10 with 4M NaOH and kept for 1 hour at 40° C. Thereafter it was neutralized to pH 7 with 4M HCl.
4. Neutralized with 4M NaOH to pH 7. The solution was made 0.1M in $NH_4Ac$ and kept at 40° C. for 1 hour. The solution was then evaporated to remove $NH_4Ac$. The residue was dissolved in 60 ml water and pH adjusted to 7.

The heparin preparations were subject to assay of anticoagulant activity (antithrombin mediated thrombin inhibition):

| Heparin preparation post nitrous acid treatment | Heparin activity IU/mg |
|---|---|
| 1. pH 7 | 121 |
| 2. pH 2.5 | 125 |
| 3. pH 10 | 116 |
| 4. pH 7, $NH_4Ac$ | 123 |

Tubing of polyethylene (2 mm i.d.) were heparinized essentially according to EP 0086186 and assayed for binding of antithrombin.

| Heparin preparation post nitrous acid treatment | AT-binding on heparinized surface $pmol/cm^2$ |
|---|---|
| 1. pH 7 | 35 |
| 2. pH 2.5 | 36 |
| 3. pH 10 | 109 |
| 14. pH 7, $NH_4Ac$ | 59 |

Conclusions

Treatment of nitrous acid oxidized heparin in an alkaline environment at pH 10 according to the present invention leads to a highly enhanced (more than 3 times higher) heparin activity after immobilisation on a surface, as compared to nitrous acid oxidized heparin treated at pH 7 according to the prior art. The activity of the heparin, before immobilisation, is not affected.

Treatment of nitrous acid oxidized heparin with $NH_4Ac$ before immobilisation results in a somewhat elevated activity, whereas treatment at low pH does not have any effects.

EXAMPLE 2

Heparin of pharmacopoeial quality was treated with nitrous acid, essentially as described in EP B-0086186 and then neutralized to pH 7 with 4M NaOH and freeze dried.

Tubing of polyethylene was heparinized with solutions of the nitrous acid oxidized heparin that had been subject to one of the following treatments.

1. No pre-treatment.
2. Dissolved in water and kept at 50° C. for 16 hours before use.
3. Dissolved in water and circulated over an aminated surface (aminated tubing) at 50° C. for 16 hours before use.

Heparinization was performed essentially as described in EP B-0086186. The heparinized pieces of tubing were analyzed with respect to binding of antithrombin.

| Heparin preparation post nitrous acid treatment | AT-binding on heparinized surface pmol/cm² |
|---|---|
| 1. No treatment | 48 |
| 2. Kept at 50° C. for 16 hours | 94 |
| 3. Kept at pH 10 and 50° C. | 109 |
| 4. Circulated at 50° C. for 16 hours over aminated surface | 122 |

Conclusion

In addition to effects observed in Example 1, treatment of nitrous acid oxidized heparin by prolonged heating or by contact with surface immobilized nucleophiles, such as amino-groups, lead to highly enhanced heparin activity when immobilized on a surface.

EXAMPLE 3

In this Example it is shown that oxidation of heparin using two different methods which are well known to a person skilled in the art, both lead to a surprising elevated AT absorption when a heparin, activated according to this invention is used.

PVC tubes with an internal diameter of 3 mm were either:
a) heparinized with a nitrous acid oxidized heparin prepared according to EP B-0086186 and not subject to further treatment,
b) heparinized with a nitrous acid oxidized heparin prepared according to EP B-0086186 and then subject to treatment with alkali (pH 10, at 40° C. for 1 h),
c) heparinized with a periodate oxidized heparin prepared according to PCT WO97/07384 and not subject to further treatment, or
d) heparinized with a periodate oxidized heparin prepared according to PCT WO97/07384 and then subject to treatment with alkali (pH 10, at 40° C. for 1 h).

|  | Not alkali treated AT absorption pmol/cm² | Alkali treated AT absorption pmol/cm² |
|---|---|---|
| Nitrous acid oxidized heparin | 46 | 105 |
| Periodate oxidized heparin | 44 | 78 |

What is claimed is:

1. A method for producing a substrate surface modification having an improved non-thrombogenic activity comprising at least the step of reacting:
   (A) functional groups on a surface to be rendered non-thrombogenic, with
   (B) heparin, modified to contain complementary functional groups, so as to form covalent bonds,
   wherein said heparin is activated to enhance its activity when surface bound, in a step before reacting (A) with (B), through a procedure selected from the group consisting of:
      (i) heating in a solvent in the range from 40° C. to the boiling temperature of the solvent;
      (ii) treatment at a pH in the range of 9–14; and
      (iii) treatment with at least one nucleophilic catalyst.

2. A method according to claim 1, where the surface to be modified is treated in one or more steps to form a layer comprising functional groups on the surface.

3. A method according to claim 1, where the pH is in the range 9–11.

4. A method according to claim 3, where the pH is 10.

5. A method according to claim 1, where the nucleophilic catalyst is ammonium acetate.

6. A method according to claim 1, where the nucleophilic catalyst contains immobilized amino-groups.

7. A method according to claim 2, which comprises forming a layer on the surface by:
   (A):
      (a) adding a layer of a polymer comprising amino groups to the surface to be modified,
      (b) optionally cross-linking the layer of step (a) with a bifunctional cross-linking agent,
      (c) adding a layer of an anionic polymer to the layer of step (b),
      (d) optionally repeating the steps (a), (b) and (c) at least one time,
      (e) followed by a final step (a), and
   (B):
      (f) modifying heparin through nitrous acid or periodate oxidation to comprise aldehyde groups,
      (g) activating the aldehyde containing heparin in a further step to enhance its activity when surface bound, said activating step (g) being selected from the group consisting of:
         (i) heating in a solvent in the range from 40° C. to the boiling temperature of the solvent;
         (ii) treatment at a pH in the range of pH 9–14; and
         (iii) treatment with at least one nucleophilic catalyst, and finally
      (h) reacting the layer resulting from step (a) or (e) with the further treated aldehyde heparin from step (g).

8. A surface modified substrate produced according to claim 2.

9. A method according to claim 2, which comprises forming a layer on the surface by
   (A):
      (a) adding a layer of a polymer comprising amino groups to the surface to be modified,
      (b) optionally cross-linking the layer of step (a) with a bifunctional cross-linking agent,
      c) adding a layer of an anionic polymer to the layer of step (b),
      (d) optionally repeating the steps (a), (b) and (c) at least one time,
      (e) followed by a final step (a), and
   (B):
      (f) modifying heparin through nitrous acid or periodate oxidation to comprise aldehyde groups,
      (g) activating the aldehyde containing heparin in a further step to enhance its activity when surface bound, said activating step (g) being selected from the group consisting of:

(i) treatment at a pH in the range of pH 9–14;
(ii) treatment with at least one nucleophilic catalyst; and
(iii) heating in the range from 40° C. to the boiling temperature of the solvent in combination with step (i) and/or step (ii).

10. A method for producing a substrate surface modification having an improved non-thrombogenic activity comprising at least the step of reacting (A) functional groups on a surface to be rendered non-thrombogenic, with (B) heparin, modified to contain complementary functional groups, so as to form covalent bonds, wherein said heparin is activated to enhance its activity when surface bound, in a step before reacting (A) with (B), through a procedure selected from the group consisting of:

(i) treatment at a pH in the range of pH 9–14;

(ii) treatment with at least one nucleophilic catalyst; and (iii) heating in the range from 40° C. to the boiling temperature of the solvent in combination with step (i) and/or step (ii).

* * * * *